United States Patent
Adachi et al.

(10) Patent No.: US 8,345,512 B2
(45) Date of Patent: Jan. 1, 2013

(54) CAPACITIVE MICROMACHINED ULTRASONIC TRANSDUCER (CMUT) DEVICE AND METHOD OF CONTROLLING THE SAME

(75) Inventors: Hideo Adachi, Iruma (JP); Katsuhiro Wakabayashi, Tokyo (JP); Kosei Tamiya, Sagamihara (JP); Masaaki Amikura, Kamiina (JP); Kazuya Matsumoto, Kamiina (JP); Ryo Ohta, Kamiina (JP); Mamoru Hasegawa, Kamiina (JP); Hiroshi Ito, Kamiina (JP)

(73) Assignees: Olympus Medical Systems Corp., Tokyo (JP); Olympus Corporation, Tokyo (JP)

( * ) Notice: Subject to any disclaimer, the term of this patent is extended or adjusted under 35 U.S.C. 154(b) by 1308 days.

(21) Appl. No.: 12/062,240

(22) Filed: Apr. 3, 2008

(65) Prior Publication Data
US 2008/0269614 A1 Oct. 30, 2008

Related U.S. Application Data

(63) Continuation of application No. PCT/JP2006/319744, filed on Oct. 3, 2006.

(30) Foreign Application Priority Data

Oct. 3, 2005 (JP) ................................. 2005-289823

(51) Int. Cl.
*A61B 8/00* (2006.01)
*B06B 1/02* (2006.01)
*H01L 41/09* (2006.01)
(52) U.S. Cl. ...................................................... 367/181
(58) Field of Classification Search .................. 367/181; 438/22, 48; 257/414
See application file for complete search history.

(56) References Cited

U.S. PATENT DOCUMENTS

| | | | |
|---|---|---|---|
| 4,391,144 A | 7/1983 | Diederichs | |
| 6,328,696 B1 | 12/2001 | Fraser | |
| 7,074,738 B2 | 7/2006 | Okubo et al. | |
| 7,589,455 B2 * | 9/2009 | Adachi et al. | 310/335 |
| 7,967,754 B2 * | 6/2011 | Knight | 600/459 |
| 2004/0039154 A1 | 2/2004 | Okubo et al. | |

(Continued)

FOREIGN PATENT DOCUMENTS

EP 1932479 A1 * 6/2008

(Continued)

OTHER PUBLICATIONS

English-language abstract only of Japanese Patent Application Publication No. 05-049638 dated Mar. 2, 1993.

(Continued)

*Primary Examiner* — Daniel Pihulic
(74) *Attorney, Agent, or Firm* — Scully, Scott, Murphy & Presser, P.C.

(57) ABSTRACT

A capacitive micromachined ultrasonic transducer (cMUT) device, comprising: a cMUT formed on a semiconductor substrate; a DC high-voltage generation unit that is provided on the semiconductor substrate and that is for generating a DC high-voltage signal to be superposed on a driving signal for the cMUT; a driving signal generation unit that is provided on the semiconductor substrate and that is for generating the driving signal; and a superposition unit that is provided on the semiconductor substrate and that is for branching the DC high-voltage signal output from the DC high-voltage generation unit and for superposing one of the branched DC high-voltage signals on the other of the branched DC high-voltage signals via the driving signal generation unit.

21 Claims, 19 Drawing Sheets

U.S. PATENT DOCUMENTS

| | | | |
|---|---|---|---|
| 2004/0174773 A1 | 9/2004 | Thomenius et al. | |
| 2005/0219953 A1* | 10/2005 | Bayram et al. | 367/178 |
| 2006/0084875 A1* | 4/2006 | Knight | 600/462 |
| 2006/0258822 A1 | 11/2006 | Okubo et al. | |
| 2007/0164632 A1* | 7/2007 | Adachi et al. | 367/140 |
| 2008/0067895 A1* | 3/2008 | Adachi et al. | 310/324 |
| 2008/0139946 A1* | 6/2008 | Adachi et al. | 600/463 |
| 2008/0269614 A1* | 10/2008 | Adachi et al. | 367/181 |
| 2011/0218442 A1* | 9/2011 | Knight | 600/459 |

FOREIGN PATENT DOCUMENTS

| | | |
|---|---|---|
| JP | 63-26341 | 5/1988 |
| JP | 3062313 | 4/2000 |
| JP | 2004-503313 | 2/2004 |
| JP | 2004-176039 | 6/2004 |
| JP | 2004-274756 | 9/2004 |
| WO | WO 01/97562 A2 | 12/2001 |
| WO | WO 2007040211 A1 * | 4/2007 |

OTHER PUBLICATIONS

I.O. Wygant et al, Integrated Ultrasonic Imaging systems Based on CMUT Arrays: Recent Progress, Proceedings of 2004 IEEE International Ultrasonics, Ferroelectrics, and Frequency Control Joint 50th Anniversary Conference, Aug. 23, 2004, vol. 1, pp. 391-394.

* cited by examiner

US 8,345,512 B2

CAPACITIVE MICROMACHINED ULTRASONIC TRANSDUCER (CMUT) DEVICE AND METHOD OF CONTROLLING THE SAME

CROSS REFERENCE TO RELATED APPLICATION

This is a Continuation Application of PCT Application No. PCT/JP 2006/319744, filed Oct. 3, 2006, which was not published under PCT Article 21(2) in English.

This application is based on and claims the benefit of priority from the prior Japanese Patent Application No. 2005-289823 filed in Japan on Oct. 3, 2005, the entire contents of which are incorporated by this reference.

BACKGROUND OF THE INVENTION

1. Field of the Invention

The present invention relates to ultrasonic transducer devices that are included in ultrasound scopes, in ultrasound miniature probes, and in ultrasound capsule endoscopes, and that are manufactured by using the micromachining processes, and also relates to a method of controlling the same.

2. Description of the Related Art

The diagnostic ultrasound method, in which ultrasound is emitted onto walls of body cavities and the state of the body is visualized on the basis of the signals echoed from the walls for making a diagnosis, is widely used. One of the instruments used for the diagnostic ultrasound method is an ultrasound endoscope scope.

An ultrasound endoscope scope has an ultrasound probe at the distal end of the insertion tube that is to be inserted into body cavities. The ultrasound probe converts electric signals into ultrasound to emit the ultrasound onto body cavities, and receives the ultrasound reflected in the body cavities in order to convert the received ultrasound into electric signals.

Conventionally, for manufacturing ultrasound probes, piezoelectric ceramics (PZT: lead-zirconate-titanate) are used as the piezoelectric device that is used for converting electric signals into ultrasound.

In recent years, capacitive micromachined ultrasonic transducers (hereinafter referred to as cMUTs) that are obtained by processing a silicon semiconductor substrate have received attention. A cMUT is one of several MEMS (Micro Electro-Mechanical System) devices.

A diagnosis modality called harmonic imaging has attracted lots of attention because it permits an ultrasonic diagnosis with a high level of accuracy that the conventional methods have never been able to attain. Accordingly, it has become essential for the body-cavity-insertion-diagnostic ultrasound systems to be compatible with this diagnosis modality. Because of this, it is desirable that ultrasonic transducers have broader bandwidths.

As is mentioned above, cMUTs that are manufactured using micromachining processes have recently received attention. The merit of cMUTs is not only that they do not contain heavy metals such as lead, but also that wide bandwidth characteristics can easily be achieved. Accordingly, cMUTs are suitable for harmonic imaging.

FIG. 1 shows an example of a conventional cMUT. The cMUT shown in FIG. 1 is the cMUT disclosed in WO 2001/097562. This ultrasonic transducer is constituted of a plurality of cMUTs. Respective cells that constitute each cMUT have a charged membrane 206. This charged membrane 206 has capacitance and is opposed to a substrate 205 that is inversely charged.

This charged membrane 206 is curved by the bias charging in the direction of the substrate 205. Also, the substrate 205 has a center that is elevated in such a manner that the elevated portion gets closer to the center of the charged membrane 206 and the density of the charged particles becomes the highest around the center of the vibration of the charged membrane 206. For the purpose of realizing the operations by using harmonics, the driving pulse waveform provided for the cells are distorted in advance. This is because the non-linear operations of devices are considered in order to reduce the harmonic components that may be generated in transmission ultrasound by a driving signal that does not have distortion.

cMUT cells can be integrated with a transducer controlling circuit such as a bias charging regulator 201 because the cMUT cells are processed by using conventional semiconductor processing methods. The cMUT cells can be processed also by using micro-stereolithography. Accordingly, the cells are formed by using various materials such as polymers and the like.

The above mentioned diagnostic ultrasound system has a high voltage-proof switch in the ultrasound probes so that it can operate at a high voltage. The diagnostic ultrasound system has a pulse generation unit and a control unit. The pulse generation unit can output pulses that have any waveforms or any voltage values. The control unit controls the output from the above high voltage-proof switch and pulse generation unit on the basis of the scanning timing of the ultrasonic transducer.

In view of the circumstances above, the present applicants suggested a method in which the DC voltage is applied only at a timing that corresponds to the application of the rf signal (Japanese Patent Application Publication No. 2004-176039).

FIG. 2 shows a first example of a method of driving an ultrasonic transducer; and this method is employed in the conventional piezoelectric transducer driving techniques. The example shown in FIG. 2 is a probe that is disclosed in Japanese Examined Patent Application No. 63-026341. This probe includes, in addition to the known circuits, an additional operation circuit in order to minimize the influence of electrical interference that can be caused by a cable that is used for connecting the probe and the ultrasound signal evaluation device and that is relatively long. In the technique disclosed in Japanese Examined Patent Application No. 63-026341, the probe includes the above described circuit; however, the circuit is not so large. Also, the operations for the ultrasound inspection are not so difficult.

The probe housing of the probe includes a transmission circuit 210. The transmission circuit 210 includes a booster coil 211, a VMOS field effect transistor (VMOS FET) 213, a control circuit 214, and a capacitor 215. The VMOS FET 213 is turned on and off in accordance with a control signal 212.

The operations of the transmission circuit 210 are explained hereinbelow. First, the capacitor 215 is charged at a high density via the booster coil 211. When the amount of the charge in the capacitor 215 reaches the upper limit, a control signal is output from the control circuit 214 to the switch driving terminal in the VMOS FET 213. Then, the VMOS FET 213 enters an ON state. Then, the discharging starts in the closed circuit of the ON state resistance, a resistor 216, and the capacitor 215. The voltage generated by this discharged current in the resistor 216 is applied to a piezoelectric transducer.

However, when a high voltage is to be induced by using this method, the booster coil 211 requires a high inductance. If the booster coil 211 has a high inductance, a resonance is caused by the capacitor 215 and the booster coil 211, and the driving pulse comes to include ringing. This ringing signal is applied to the piezoelectric transducer without being reduced or blocked, which causes deterioration in the spatial resolution and the S/N ratio.

FIGS. 3A and 3B show a second example of a method of driving a piezoelectric ultrasonic transducer that is employed in the conventional techniques. FIG. 3A shows a diagnostic ultrasound system disclosed in Japanese Patent No. 3062313. FIG. 3B shows the same system in a simplified manner. Japanese Patent No. 3062313 discloses a configuration for minimizing the influence of the electric interference caused by a long connection cable although the technique disclosed in this document is not intended to have a countermeasure against the above ringing.

In FIGS. 3A and 3B, an ultrasound probe 220 and a diagnostic ultrasound system 221 are shown. Ultrasound signals are emitted and received by an ultrasonic transducer 222 provided in the ultrasound probe in order to perform the ultrasound scan on the subject. The diagnostic ultrasound system 221 can obtain an ultrasound sectional image on the basis of the received ultrasound signals.

In the ultrasound probe 220, a high voltage-proof switch 223 is provided. In the above diagnostic ultrasound system 221, a pulse generation unit 227 and a control unit 228 are provided. The pulse generation unit 227 can output a pulse that has any voltage value in any waveform. The control unit 228 controls the output of the voltage-proof switches 223 and the pulse generation unit 227 in accordance with the timing of the scan performed by the ultrasonic transducer.

By the above configuration, the size of the electric circuit in the ultrasound probe is reduced. Also, high voltage pulse signals for driving the ultrasonic transducer can be generated efficiently in the probe. Also, excellent ultrasound images that are not influenced by the interference caused by the cable can be obtained, and noise that leaks to the external environment can be reduced. Also, the ringing is not caused because there is no element that can cause resonation in the circuit.

As described above, it is proposed to produce a micro piezoelectric transformer and a micro electromagnetic transformer and to arrange them close to a cMUT and a pMUT (a piezoelectric transducer that is produced by using the micromachining processes).

SUMMARY OF THE INVENTION

A cMUT device according to the present invention comprises:
a cMUT formed on a semiconductor substrate;
a DC high-voltage generation unit that is provided on the semiconductor substrate and that is for generating a DC high-voltage signal to be superposed on a driving signal for the cMUT;
a driving signal generation unit that is provided on the semiconductor substrate and that is for generating the driving signal; and
a superposition unit that is provided on the semiconductor substrate and that is for branching the DC high-voltage signal output from the DC high-voltage generation unit and for superposing one of the branched DC high-voltage signals on the other of the branched DC high-voltage signals via the driving signal generation unit.

A method of controlling a cMUT device according to the present invention comprises:
a cMUT formed on a semiconductor substrate;
a DC high-voltage generation unit that is provided on the semiconductor substrate and that is for generating a DC high-voltage signal to be superposed on a driving signal for the cMUT;

a first switching unit switching output levels of the DC high-voltage signal output from the DC high-voltage generation unit;
driving signal generation unit that is provided on the semiconductor substrate and that is for generating the driving signal;
a superposition unit that is provided on the semiconductor substrate and that is for superposing the driving signal on the DC high-voltage signal;
a second switching unit that is provided on the semiconductor substrate and that controls the driving signal or the DC high-voltage signal, which is input into the superposition unit; and
a third switching unit that is provided on the semiconductor substrate and that controls an ultrasonic reception signal being converted into an electric signal by the cMUT and controls the converted electric signal, which is output to an external environment, in which:
if ultrasound is to be transmitted from the cMUT device, the first switching unit is driven, and the output level of the DC high-voltage signal is set;
the driving signal generation unit is driven and the driving signal is generated;
the second switching unit is driven so that the driving signal and the DC high voltage signal are input into the superposition unit; and
the third switching unit is caused to be in an OFF state.

BEST MODES FOR CARRYING OUT THE INVENTION

Conventionally, miniature piezoelectric transformers and miniature electromagnetic transformers are produced in a discrete manner and are arranged close to cMUTs and pMUTs. However, in this method, the size of electric circuits can only be reduced to some extent, and a high level of quality management is required because of complicated wiring and connection.

Meanwhile, to form a high-voltage generation unit on or in a silicon substrate that is the same as an ultrasonic transducer produced by using the micromachining process has not been suggested conventionally.

Accordingly, by using the micromachining process or the semiconductor integration process, in the present invention, a DC high-voltage generation unit is formed on or in a silicon substrate that is the same as an ultrasonic transducer produced by using the micromachining process. Thereby, the reduction of the size of the cMUT devices is realized.

In other words, in a cMUT according to the present invention, DC high-voltage generation unit and devices such as a semiconductor switch, a charge amplifier, or the like are arranged in an integrated manner close to the capacitive ultrasonic transducer on a semiconductor substrate. Accordingly, the reduction of the size of the cMUT devices is realized.

Figure 1:
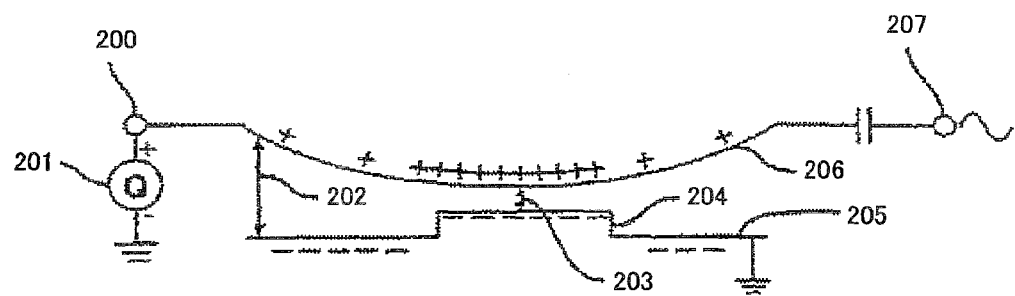
FIG. 1 shows an example of a conventional cMUT.
Figure 2:
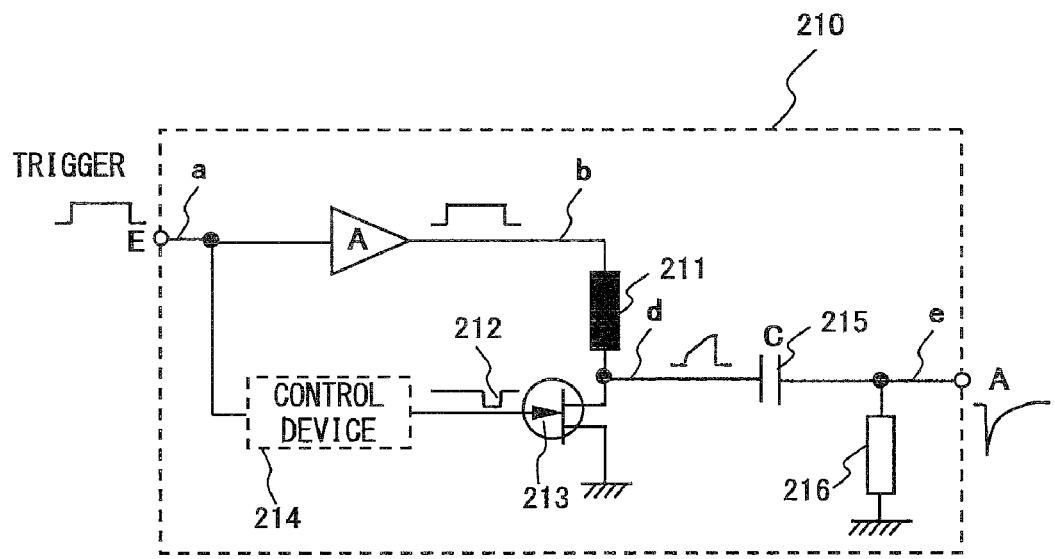
FIG. 2 shows a first example of a method of driving an ultrasonic transducer that is employed in the conventional techniques.
Figure 3A:
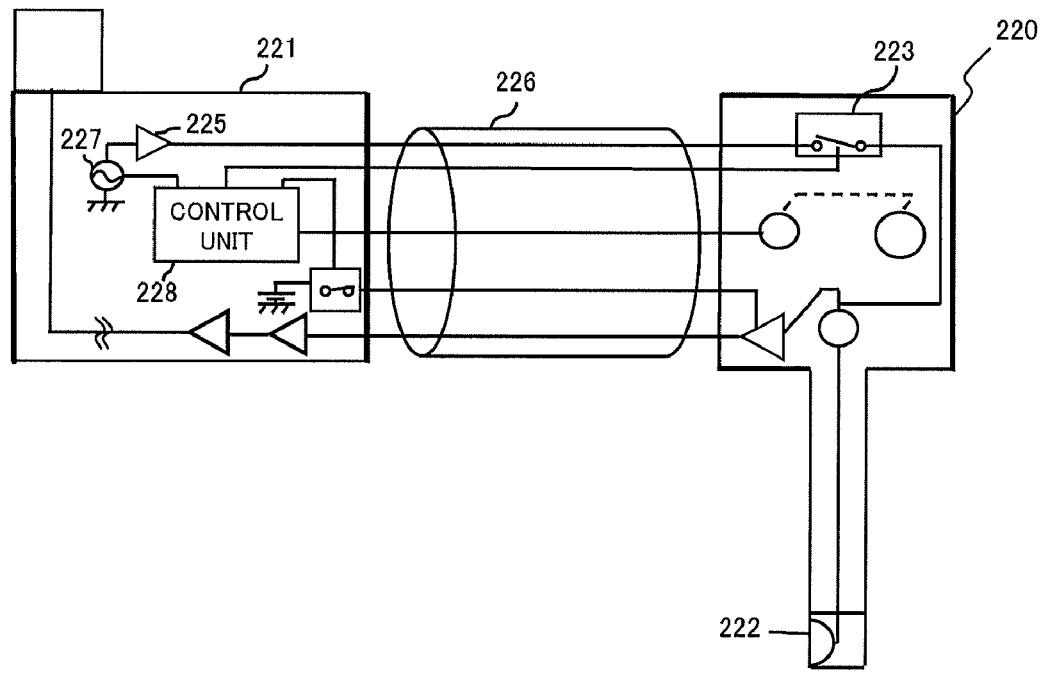
FIG. 3A shows a second example of a method of driving an ultrasonic transducer that is employed in the conventional techniques.
Figure 3B:
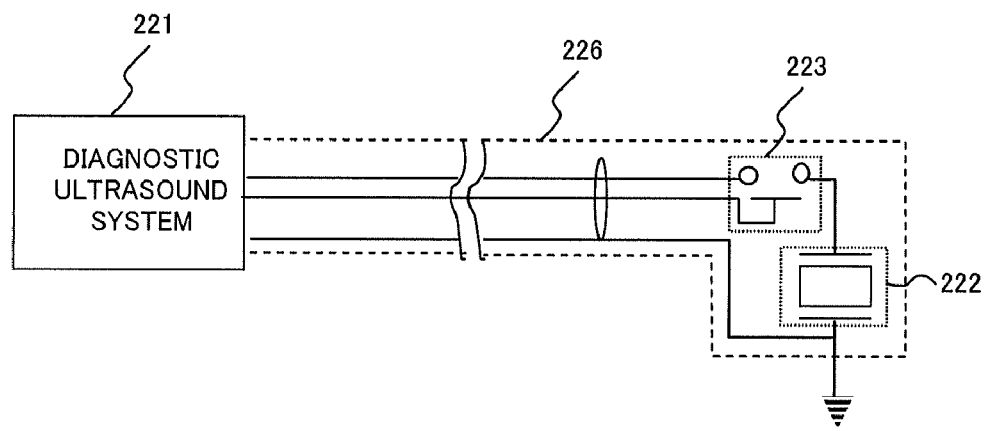
FIG. 3B shows in a simplified manner the system shown in FIG. 3A.
Figure 4:
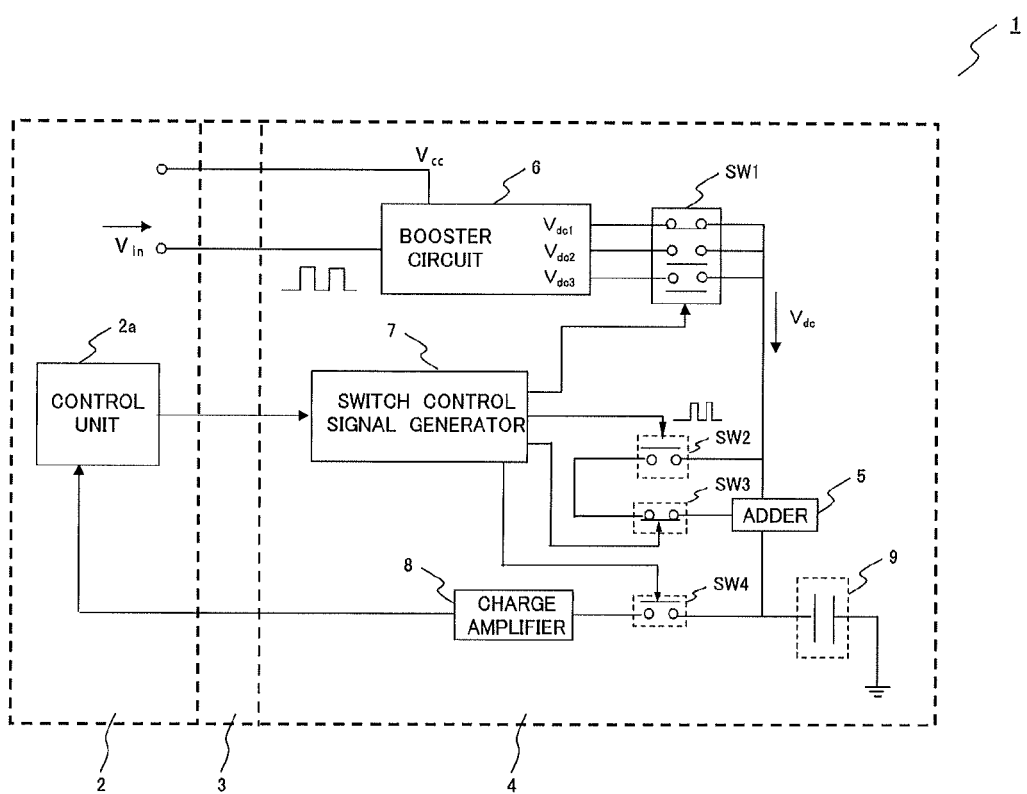
FIG. 4 shows a configuration of a transmitting and receiving circuit system for body-cavity-insertion diagnostic ultrasound system according to the present embodiment.

FIG. 4 shows a configuration of a body-cavity-insertion diagnostic ultrasound system according to the present embodiment. The body-cavity-insertion diagnostic ultrasound system 1 has at least a signal controlling system 2 and an insertion tube (the insertion tube mainly consisting of a bending section, a flexible tube 3, and an ultrasound probe 4).

The diagnostic ultrasound system 2 has a control unit 2a. The control unit 2a controls the operations of a switch control signal generator 7 and performs signal processing on the ultrasonic reception signal transmitted from the ultrasound probe 4 via the bending section and the flexible tube 3 in order to convert the process signals into image signals.

The insertion tube is shaped as a long tube because it is inserted into body cavities. The ultrasound probe 4 has a cMUT 9 as an ultrasonic transducer. This cMUT 9 transmits and receives ultrasonic signals. The bending section is located at the back side of the ultrasound probe 4 and can be bent as necessary. The flexible tube is located at the back side of the bending section, and is long, narrow, and flexible. The insertion tube includes a bundle of coaxial cables used for the respective transducer elements that constitute the cMUT 9.

The ultrasound probe 4 includes switches SW1 through SW4, an adder 5, a booster circuit 6, a switch control signal generator 7, a charge amplifier 8, and the cMUT 9. The booster circuit 6 is a capacitive booster element that is formed on the semiconductor substrate by using the micromachining process. It is also possible to further form the adder 5, the switch control signal generator 7, the charge amplifier 8, and the cMUT 9 on the semiconductor substrate that is the same as this capacitive booster element by using the micromachining process or other semiconductor integration processes. Thereby, it becomes possible to make the ultrasound probe 4 smaller.

A cMUT array (cMUT 9) has a configuration in which a plurality of ultrasonic transducer elements (or simply "elements") that serve as the minimum unit for inputting and outputting drive control signals are arranged. Each of these elements consists of vibrators that are called transducer cells (or simply "cells"). The cell is a component that constitutes one cavity (blank space), as will be described later.

The switch control signal generator 7 generates control signals used for turning ON/OFF the switches SW1 through SW4. In other words, the switch control signal generator 7 generates signals that determine timings at which the respective switches are turned ON/OFF and determine periods during which the switches are in an ON/OFF state. Each of the switches SW1 through SW4 is made of a DMOS (Double Diffused MOSFET) or a VMOS (V-groove MOSFET).

The adder 5 superposes the driving pulses for driving the cMUT 9 on the DC voltage boosted by the booster circuit 6. The driving pulses are generated by the switch SW2.

The charge amplifier 8 has a function of performing impedance conversion (conversion from a high impedance to a low impedance), a function of detecting electric charges on the surface of the electrodes in the cMUT 9, and a function of amplification. The function of detecting the electric charges is a function of detecting the electric charges that changes on the upper electrode in response to the vibrations of the membrane corresponding to the intensity of the echo signals received in the cMUT 9.

Next, the operations of the body-cavity-insertion diagnostic ultrasound system 1 will be explained. First, the transmission of ultrasound beams is explained.

When transmitting ultrasound beams, the switch control signal generator 7 turns on the switch SW3, and turns off the switch SW4.

Next, voltage $V_{in}$ and voltage $V_{CC}$ are input into the booster circuit 6. Here, voltages $V_{in}$ and $V_{CC}$ are explained. There is a method of generating $V_{CC}$ by transmitting the alternating-current voltage $V_{in}$ in the coaxial cable in the insertion tube and providing a rectifier circuit in the booster circuit 6, and a method of generating $V_{in}$ by transmitting the DC voltage $V_{CC}$ in the coaxial cables and providing an oscillator circuit in the booster circuit. In both methods, the voltages transmitted in the coaxial cables are much smaller than the cMUT driving voltage.

The booster circuit 6 generates a DC voltage $V_{dc}$ that is obtained by boosting the voltages $V_{in}$ and $V_{CC}$, and outputs this DC voltage $V_{dc}$ to the switch SW1. In the present embodiment, the booster circuit 6 outputs three steps of the DC voltages $V_{dc}$ ($V_{dc1} < V_{dc2} < V_{dc3}$) obtained on the basis of the different levels of boosting.

The switch SW1 can perform switching of, for example, three channels in the present embodiment. The switch SW1 switches these channels on the basis of the control signals of the switch control signal generator 7, and outputs one of the DC voltages $V_{dc}$ ($V_{dc1}$, $V_{dc2}$, $V_{dc3}$) output from the booster circuit 6.

Also, the switch control signal generator 7 generates pulses used for driving the cMUT 9 on the basis of the cable transmission signals transmitted from the control unit 2a of the diagnostic ultrasound system 2. Then, the switch control signal generator 7 outputs these pulses to the switch SW2. The switch SW2 performs the ON/OFF operations on the basis of the pulses, and superposes the driving pulses on the DC voltage $V_{dc}$ via the switch SW3 and the adder 5.

The superposed driving signals are output to the cMUT 9. In the cMUT 9, a high voltage is applied to a pair of electrodes consisting of the upper electrode and the bottom electrode, and thereby these electrodes attract each other, and when the applied voltage becomes zero, the electrodes return to their original positions. This vibration of the membrane generates ultrasound, and the ultrasound is emitted in the upward direction of the upper electrode.

Next, reception of ultrasound beams will be explained. When receiving the ultrasound beams, the switch control signal generator 7 turns off the switch SW3, and turns on the switch SW4.

The ultrasound emitted from the cMUT 9 is reflected in body cavities. Then, the reflected wave is received by the cMUT 9. The cMUT 9 converts the received reflected wave into electric signals. The reception signals converted into the electric signals are transmitted to the diagnostic ultrasound system 2 via the charge amplifier 8. The diagnostic ultrasound system 2 forms diagnostic ultrasound images on the basis of the reception signals.

Next, the booster circuit 6 will be explained by referring to FIGS. 5 and 6.

Figure 5:
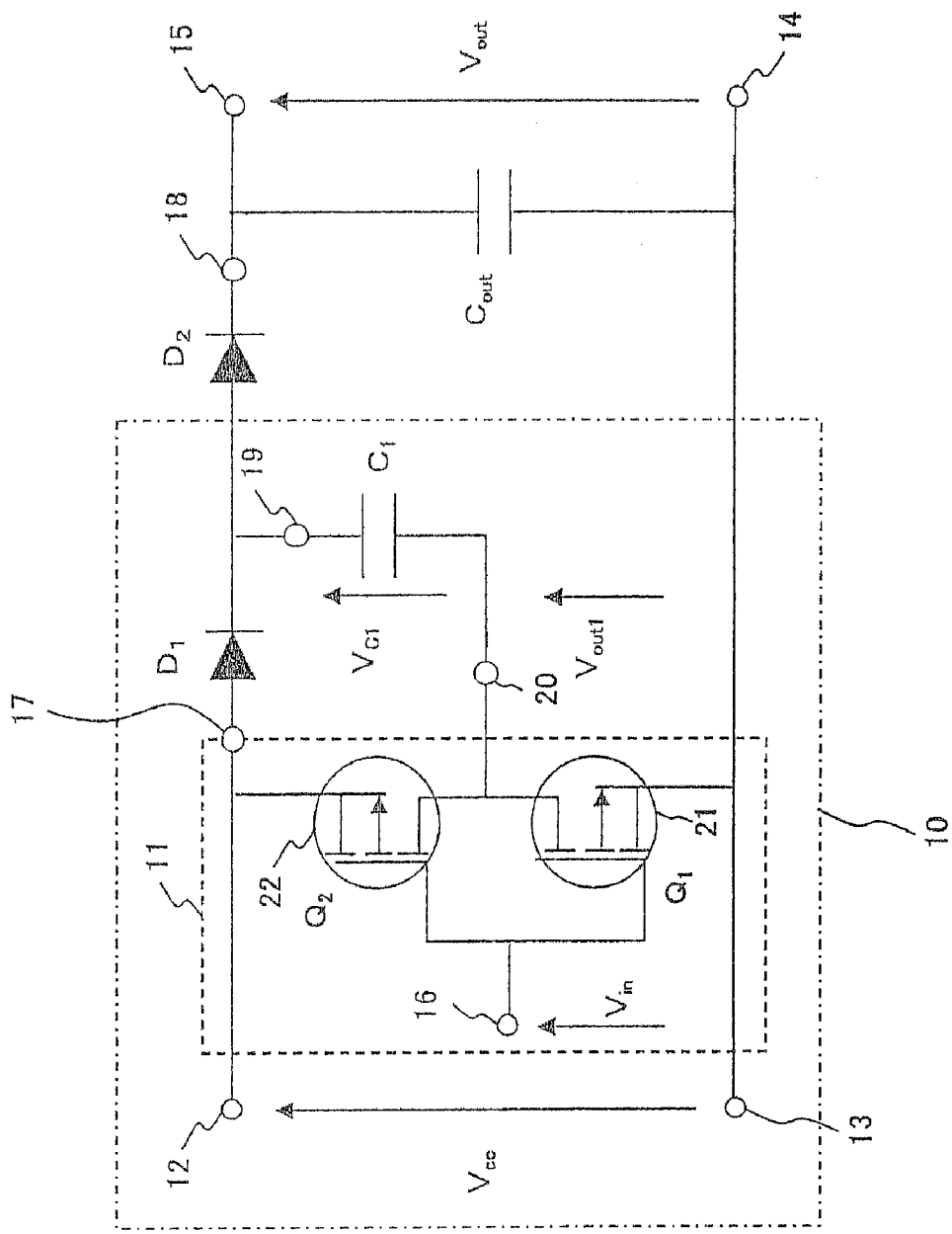
FIG. 5 shows the principle of a booster circuit 6 according to the present embodiment.

FIG. 5 shows the principle of the booster circuit 6 according to the present embodiment. The circuit shown in FIG. 5 includes a Schmidt Trigger inverter 11, capacitors $C_1$ and $C_{out}$, diodes $D_1$ and $D_2$ and terminals 12 through 20. The Schmidt Trigger inverter 11 includes a CMOSFET (Complementary Metal Oxide Semiconductor Field Effect Transistor) 21 ($Q_1$) and a CMOSFET 22 ($Q_2$).

Next, the operation principle of the circuit shown in FIG. 5 will be explained. A rectangular wave $V_{in}$ of $10V_{op}$ is applied, at a frequency of e.g., 7.5 MHz, to a common gate connection terminal 16 of $Q_1$ and $Q_2$ that perform the push-pull operations ($V_{CC}$ is also 10V).

When 10V is applied to the common gate connection terminal 16, $Q_1$ is ON and $Q_2$ is OFF. Then, the diode $D_1$ receives the forward bias, and the voltages $V_{c1}=V_{CC}-V_D$ ($V_D$ is the forward voltage drop of the diode $D_1$, and $V_D$ is at most 0.7V) is applied to the capacitor $C_1$.

Meanwhile, the capacitor $C_{out}$ is charged, and the voltage of $V_{out}=V_{CC}-2V_D$ is accumulated in the capacitor $C_{out}$. Also, the diode $D_2$ receives the forward bias (the forward voltage drop of the diode $D_2$ is also $V_D$, and $V_D$ is at most 0.7V).

Next, when $V_{in}=0$, $Q_1$ becomes OFF, and $Q_2$ becomes ON, and the diode $D_1$ receives the reverse bias; accordingly, a voltage is supplied to the negative terminal of the capacitor $C_1$. Then, $C_{out}$ is charged via the diode $D_2$ receiving the forward bias. In other words, as a result of the positive terminal of the capacitor $C_1$ being boosted, a voltage higher than the supplied voltage $V_{CC}$ can be obtained.

When the capacitance of the capacitor $C_{out}$ is smaller than the capacitance of the capacitor $C_1$, the equation $V_{out}=V_{out1}+V_{c1}=2(V_{in}-V_D)$ is satisfied (where $V_{out1}$ is the forward voltage drop of). When $V_{CC} \gg V_D$, $V_{out}$ nearly equals $2V_{in}$, and the circuit shown in FIG. 5 operates as a voltage-doubler booster circuit.

As described above, it is desirable to make the capacitance of the capacitor $C_1$ larger than the capacitance of the capacitor $C_{out}$. Accordingly, a high dielectric capacitor is used as the capacitor $C_1$. This high dielectric capacitor consists of a ferroelectric thin film. The ferroelectric substance is a substance that has electric polarization even when an electric field is not applied from the external environment, and in this substance this polarization (spontaneous polarization) can be inverted by an electric field applied from the external environment.

A typical example of a ferroelectric substance is a crystal having a perovskite structure. When the alternating voltage is applied to ferroelectric substances, the polarization represents the hysteresis curve. $SrBi_2(Nb_{1-x}Ta_x)_2O_9$ is a ferroelectric substance. This $SrBi_2(Nb_{1-x}Ta_x)_2O_9$ is a highly durable ferroelectric material, and has a bismuth layer structure.

Also, the ferroelectric substance may be formed of a solid solution thin film consisting of one or both of $BaTiO_3$ and $SrTiO_3$. Also, the high dielectric substance may be formed of a dielectric thin film that does not contain heavy metals, and the dielectric thin film can be formed of high dielectric materials such as $ZnO$, $AlN$, $Ta_2O_5$, or the like. These dielectric materials are environmentally friendly because they do not contain heavy metals.

Figure 6:
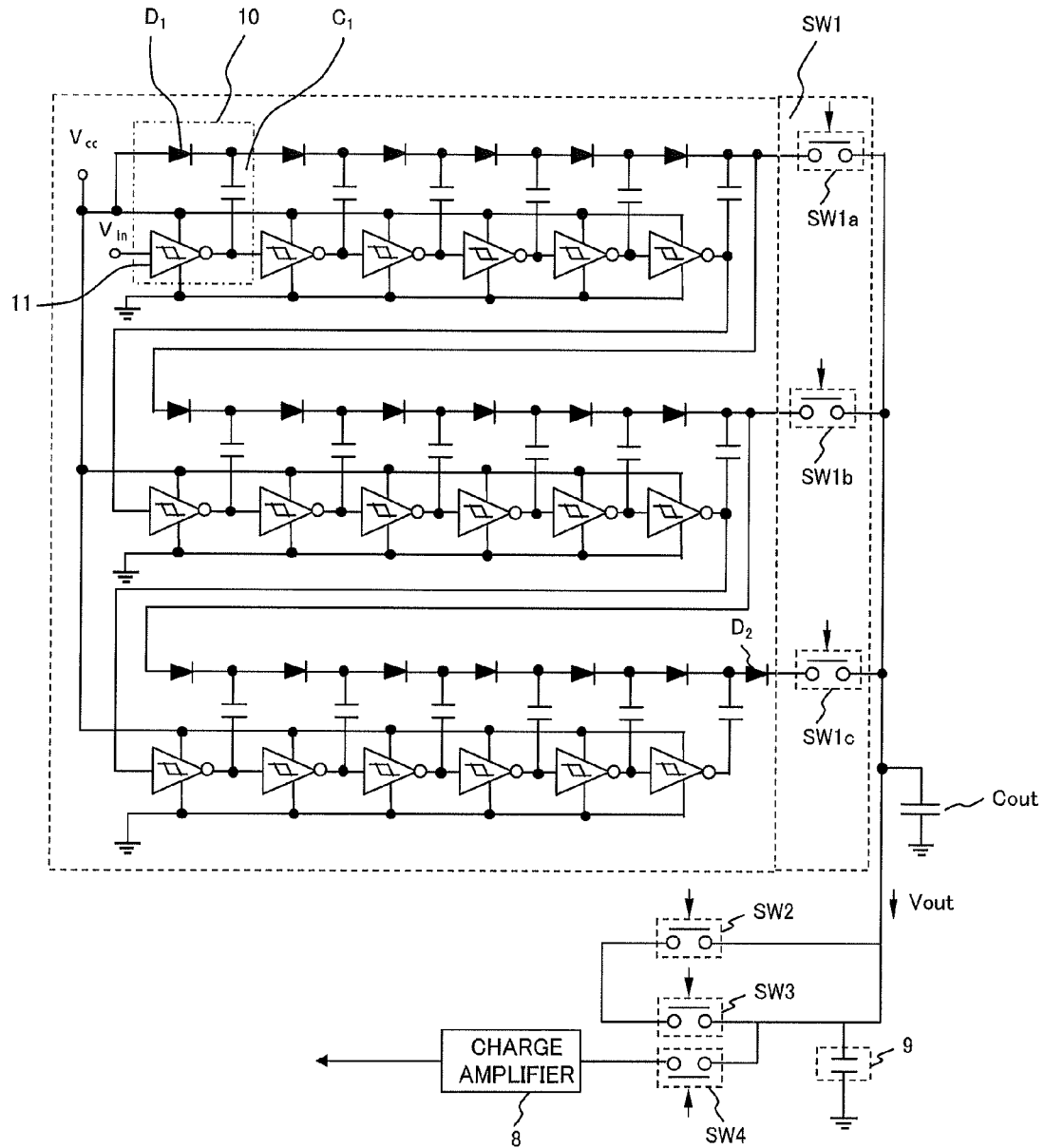
FIG. 6 shows the configuration of the booster circuit 6 according to the present embodiment.

FIG. 6 shows the concept of the configuration of the booster circuit 6 according to the present embodiment. The booster circuit 6 includes N (N is a positive integer) number of circuits 10 shown in FIG. 5 in a cascade connection. When N number of circuits 10 are in a cascade connection, the voltage $V_{out0}$ output from the Nth circuit can be expressed by the equation below. Accordingly, by changing the number of circuits 10 to be in a cascade connection, the level of voltage boosting can be controlled.

$$V_{out}=(N+1)(V_{CC}-V_D)$$

When $V_{CC} \gg V_D$, $V_{out}$ nearly equals $(N+1)V_{CC}$

In FIG. 6, the switch SW1 has three channels (SW1a, SW1b, and SW1c). When SW1a=ON, SW1b=OFF, and SW1c=OFF, the six circuits 10 are in a cascade connection, and accordingly the equation $V_{out}=7 (V_{CC}-V_D)$ (when $V_{CC} \gg V_D$, $V_{out}$ nearly equals $7V_{CC}$) is satisfied. When SW1a=OFF, SW1b=ON, and SW1c=OFF, twelve circuits 10 are in a cascade connection, and accordingly the equation $V_{out}=13 (V_{CC}-V_D)$ (when $V_{CC} \gg V_D$, $V_{out}$ nearly equals $13V_{CC}$) is satisfied. When SW1a=OFF, SW1b=OFF, and SW1c=ON, eighteen circuits 10 are in a cascade connection, and accordingly the equation $V_{out}=19 (V_{CC}-V_D)$ (when $V_{CC} \gg V_D$, $V_{out}$ nearly equals $19V_{CC}$) is satisfied.

As described above, by using a booster circuit, the input voltage $V_{CC}$ can be boosted to about (N+1) times the value that would be obtained without a booster circuit. Further, it becomes possible to generate a DC high voltage from a low voltage.

When ultrasound beams are transmitted, the switch SW3=ON, and the switch SW4=OFF. Then, by using the switch SW2, the RF high-voltage driving signal is superposed on the boosted DC high voltage, and the superposition signal is applied to the bottom electrode in the cMUT. The RF high-voltage driving signal is obtained by branching the DC high-voltage signal and by turning on and off the switch SW2 with respect to the branched signals at a high speed. Then, by performing the additional superposition on the RF high-voltage driving signal and the DC high voltage by using the adder 5, the superposition signal to be applied to the cMUT 9 is obtained. Additionally, the frequency of the ultrasound to be transmitted from the cMUT is determined by the ON/OFF frequency of SW2.

The cMUT 9 to which the high-voltage superposition signal is applied emits ultrasound from its membrane surface that is provided on the upper electrode. The emitted ultrasound is reflected from the living-body tissue, and the reflection wave is received by the cMUT 9.

When ultrasound beams are received, switch SW3=OFF and switch SW4=ON. The cMUT 9 converts the reflection ultrasonic wave into electric signals. The reception signals that have been converted into electric signals are sent to the diagnostic ultrasound system 2 via the charge amplifier 8. The diagnostic ultrasound system 2 forms diagnostic ultrasound images on the basis of the reception signals.

By using the booster circuit 6, only a low-voltage signal is transmitted through the cables, and thereby it becomes possible to efficiently generate high-voltage pulses on which the DC bias voltage for driving the ultrasonic transducer is superposed in the probe. Also, it becomes possible to avoid the effect of noise caused by the cables.

Figure 7:
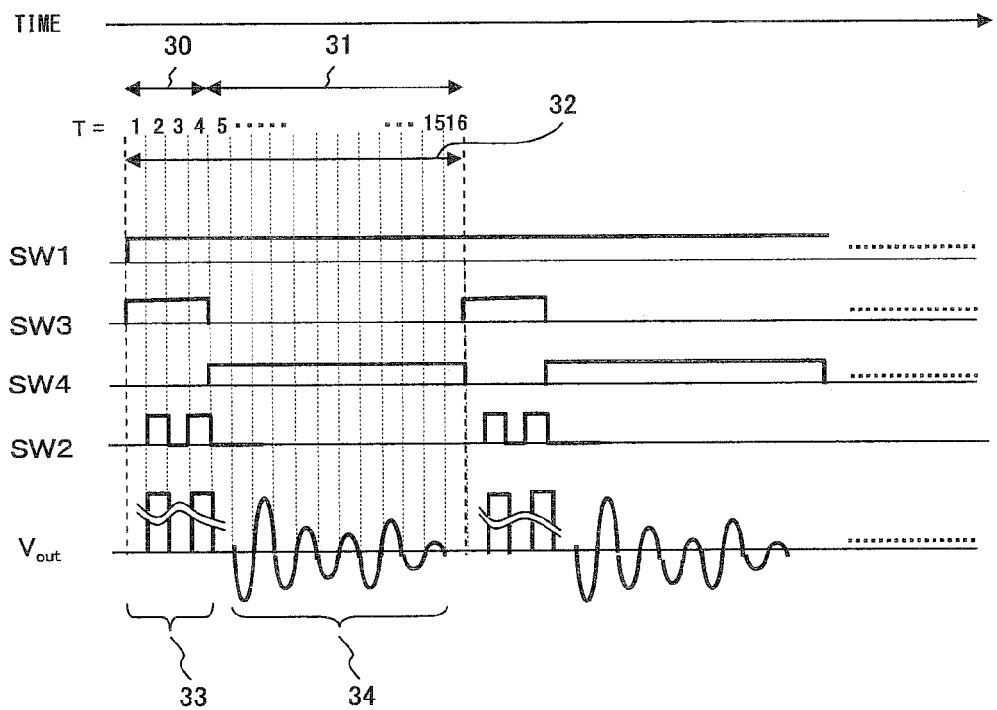
FIG. 7 is a timing chart showing the operations of switches (SW), driving and received voltage signals for transmitting and received ultrasound.

FIG. 7 is a timing chart showing the operations of the switches (SW) and driving voltage signals for transmitting ultrasound. FIG. 7 will be explained with reference to FIG. 4. FIG. 7 shows an ultrasound transmission period 30 and an echo signal reception period 31. A period that consists of the ultrasound transmission period 30 and the echo signal reception period 31 is repeated. T (=1 through 4) represents the transmission period.

When the timing T=1, SW3 becomes ON. Then, SW4 is in an OFF state. Then, SW1 becomes ON (strictly, one of SW1a, SW1b, and SW1c becomes ON). Then, the $V_{in}$ and $V_{CC}$ are input into the booster circuit 6, and the DC voltage $V_{dc}$ that is at a high-voltage level is output from the booster circuit 6.

When the timing T=2, SW2 becomes ON. Then, the ON voltage $V_{dc}$ of SW2 is further additionally superposed on the DC voltage $V_{dc}$, and is applied to the cMUT 9.

When the timing T=3, SW2 becomes OFF. Then, the ON voltage $V_{dc}$ of SW2 is blocked, and accordingly the voltage applied to the cMUT 9 is $V_{dc}$.

T=4 and T=5 are respectively repeats of the operations of T=1 and T=2.

As described above, variations are caused between $2V_d$, and $V_{dc}$ at a high speed. In other words, a high voltage superposition driving signal voltage $V_{drv}$ whose amplitude is $V_{dc}$ and whose DC bias voltage is $1.5V_{dc}$ is generated, and this is applied to the cMUT 9, and the cMUT 9 emits ultrasound.

T=5 through T=16 are the echo signal reception periods. Numeral 34 denotes the waveform of the echo reception signal, and the cycle thereof is approximately equal to the cycle of turning ON and OFF SW2. During the echo signal reception periods, SW3 is in an OFF state, SW4 is in an ON state, and the cMUT 9 receives the ultrasound reflected by the living-body tissue. The ultrasound received by the cMUT 9 is converted into electric signals, and is output to the diagnostic ultrasound system 2 via the SW4 and the charge amplifier 8.

The above explanation is about one element of the cMUT; however, the scope of the present invention is not limited to this explanation. For example, even in the case of one-dimensionally or two-dimensionally arranged array of elements, a number of control channels corresponding to the number of the elements can be configured. Also, by providing a phase difference for each control channel for controlling the timing of the driving of the SW arranged on each control channel, it becomes possible for the transmission beam to be formed. Further, by performing the reception beam forming process on the output from the plurality of the charge amplifiers 8, a linear scan or a sector scan can be performed accurately.

Next, the configuration in which the cMUT according to the present embodiment and the driving control circuit formed in a monolithic manner are integrated will be explained.

Figure 8:
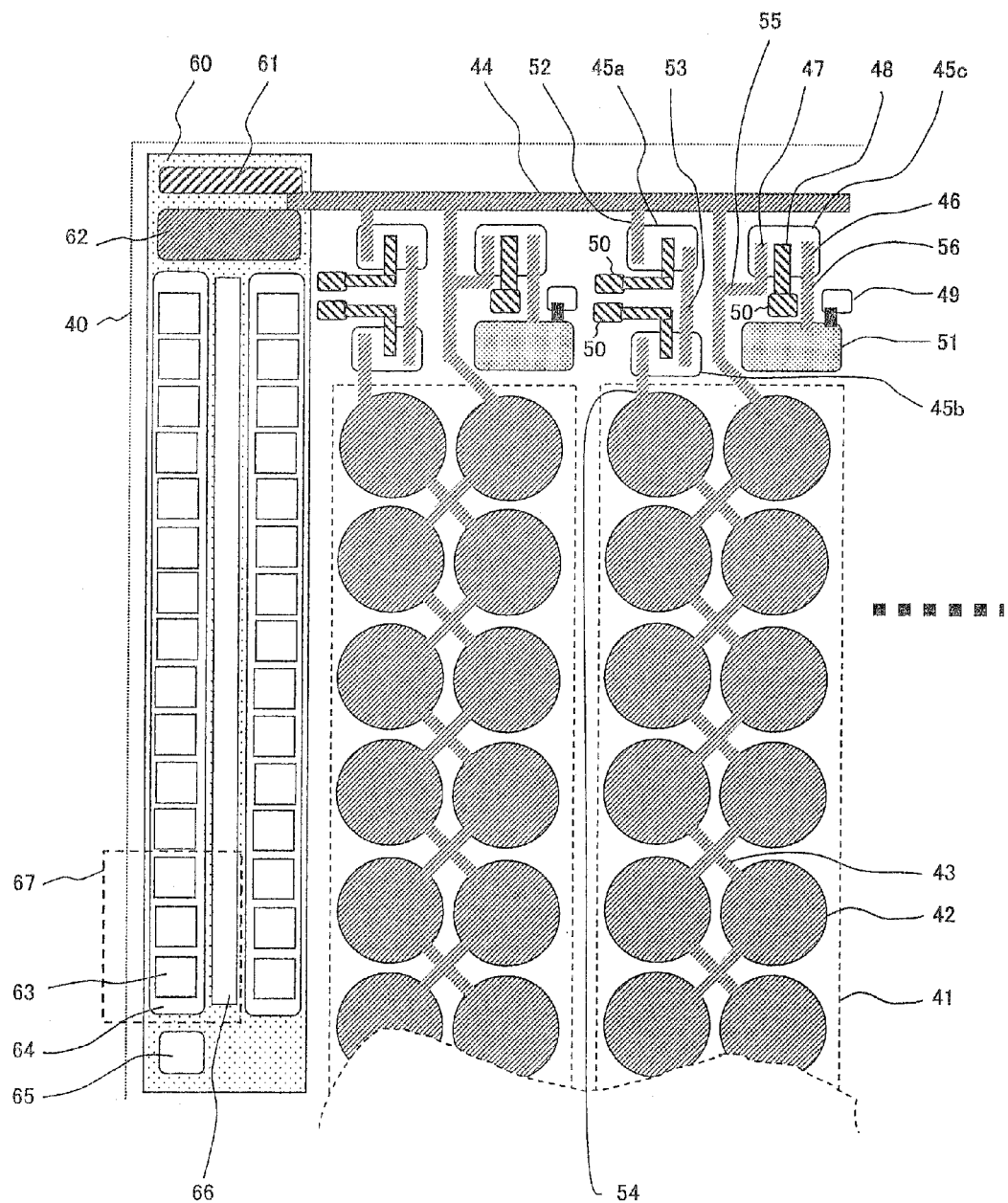
FIG. 8 shows an example of a plan view of the cMUT 9 according to the present embodiment.

FIG. 8 shows an example of a plan view of the cMUT 9 according to the present embodiment. In FIG. 8, a plurality of cMUT elements 41 are arranged in a parallel connection on a cMUT chip 40. A plurality of bottom electrodes 42 are formed on each of the cMUT elements 41. The portion expressed as the bottom electrodes 42 corresponds to the cMUT cells. When the membranes of the respective cMUT cells vibrate, ultrasound is emitted.

The respective bottom electrodes 42 are connected to one another via a interconnections 43. On the upper portion of the cMUT chip 40, a wire 44 for supplying DC is arranged, and is connected to the bottom electrodes 42 arranged on the end of the respective cMUT elements 41.

In FIG. 8, on a region between the wire 44 and the cMUT elements 41, MOSFET (Metal Oxide Semiconductor Field Effect Transistor) switches 45 (45a, 45b, and 45c) and a charge amplifier 51 are provided.

The drain region of the MOSFET switch 45a and the wire 44 are connected to each other via a wire 52. The source region of the MOSFET switch 45a and the drain region of the MOSFET switch 45b are connected to each other. The source region of the MOSFET switch 45b and the bottom electrode 42 are connected to each other via a wire 54. The drain region of the MOSFET switch 45c, the wire 44, and the bottom electrode 42 are connected to one another via a wire 55. The source region of the MOSFET switch 45c and a charge amplifier 51 are connected to each other via a wire 56. Electrode pads 50 (50a, 50b, and 50c) for inputting Gate signal are provided on the respective MOSFET switches 45 (45a, 45b, and 45c).

The MOSFET switches 45a, 45b, and 45c respectively correspond to the switches SW2, SW3, and SW4 shown in FIG. 4. In FIG. 8, the adder 5 that is shown in FIG. 4 is omitted.

The region on the left side of FIG. 8 (a booster circuit region 60) corresponds to the booster circuit 6 shown in FIG. 4. The booster circuit 60 consists of a capacitor region 61 (corresponding to the capacitor $C_{out}$ shown in FIG. 5), an switching region 62 for switching output voltage (corresponding to the switch SW1 shown in FIG. 4), an upper electrode 63 on a high-capacitance capacitor (corresponding to the capacitor $C_1$ shown in FIG. 5), a high dielectric thin film 64 (corresponding to the capacitor $C_1$ shown in FIG. 5), an electrode pad 65 for inputting a signal (corresponding to the electrode pad to which $V_{in}$ shown in FIG. 5 is input), and a Schmidt Trigger inverter circuit+diode region 66 (corresponding to the Schmidt Trigger inverter 11 and the diodes $D_1$ and $D_2$).

Figure 9:
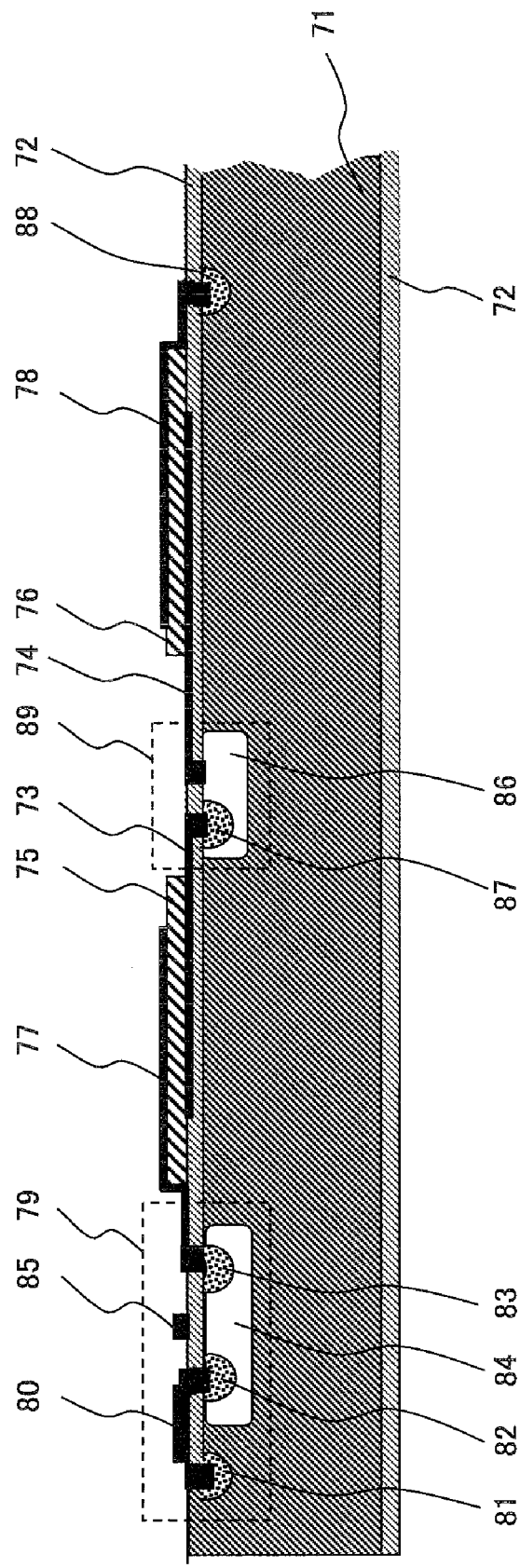
FIG. 9 shows an example of a sectional view of a booster circuit region according to the present embodiment.

FIG. 9 shows an example of a sectional view of the booster circuit region according to the present embodiment. FIG. 9 shows a view that corresponds to a sectional view of the booster circuit region 60 shown in FIG. 8. The booster circuit region shown in FIG. 9 has the same functions as that in FIG. 8 although the arrangement is partially changed from the arrangement in FIG. 8 for the purpose of explanation.

In FIG. 9, the booster circuit region consists of a silicon substrate 71, a surface oxide film 72, bottom electrodes 73 and 74, high dielectric materials 75 and 76, upper electrodes 77 and 78, a CMOS converter circuit (CMOS FET+diode) 79, a ground wire 80, diffusion-regions-for-ohmic-contact 81 and 88, a MOSFET source region 82, a MOSFET drain region 83, a MOSFET channel region 84, a MOSFET gate wire 85, a diode-p-diffusion region 86, an n-diffusion region 87, and a diode region 89. Hereinafter, this configuration is explained.

FIG. 9 includes the silicon substrate 71 having thereon large capacitance thin film capacitors (or high dielectric constant materials 75 and 76, 75 and 76 respectively correspond to the capacitors $C_1$ and $C_{out}$ in FIG. 5) and the surface oxide film 72, the bottom electrodes 73 and 74, and the upper electrodes 77 and 78.

The Schmidt Trigger inverter 79 (corresponding to the Schmidt Trigger inverter 11 in FIG. 5) that constitutes the voltage-doubler booster circuit and the diode region 89 (corresponding to the diodes $D_1$ and $D_2$ shown in FIG. 5) are formed on the silicon substrate 71.

In the Schmidt Trigger inverter 79, two MOSFETs (corresponding to the CMOSFET 21 ($Q_1$) and the CMOSFET 22($Q_2$) in FIG. 5) each consisting of the source region 82, the drain region 83, and the channel region 84 are complementarily connected to each other as shown in FIG. 5 (in FIG. 9, CMOSFET 21 ($Q_1$) of the above two MOSFETs is omitted).

The channel region 84 corresponding to the CMOSFET 22 ($Q_2$) is connected in such a manner that the source side has the same potential via the diffusion-region 81 of the silicon substrate 71. The upper electrode 78 of one capacitor is connected to the silicon substrate 71 via the diffusion-region 88 in such a manner that the upper electrode 78 has the same potential.

When the silicon substrate 71 is grounded, the ground wire 80 and the upper electrode 78 are also grounded. $V_{in}$ shown in FIG. 5 is input into the MOSFET gate wire 85. Further, when the upper electrode 78 is not a voltage-doubler booster circuit of the final stage, the upper electrode 78 is connected to the output unit of the Schmidt Trigger inverter of the next stage as shown in FIG. 6, so that it will not cause the upper electrode 78 to have the same potential as that of the silicon substrate 71.

Figure 10:
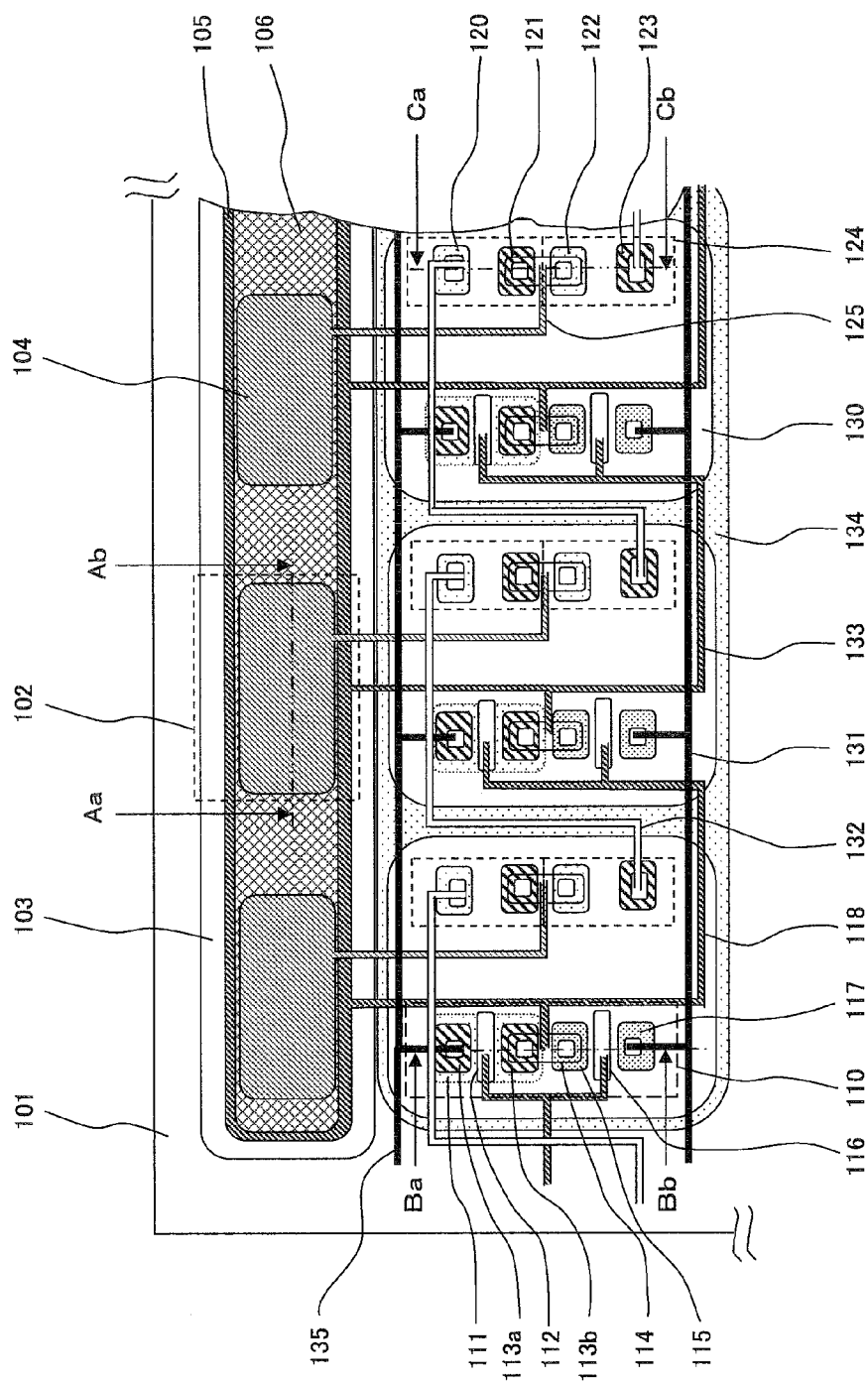
FIG. 10 shows an example of a plan view of the booster circuit region according to the present embodiment.

FIG. 10 shows an example of a plan view of the booster circuit region according to the present embodiment. FIG. 10 is an enlarged view showing a region 67 enclosed by a dashed line in FIG. 8. On a silicon substrate 101, a plurality of ferroelectric thin film capacitors (FECs) 102 are formed. Also, on the FEC 102, a p+ diffusion region 134 is formed. On this p+ diffusion region 134, a plurality of n diffusion regions 130 are formed. On each of the n diffusion regions 130, a CMOS inverter 110 and a pn junction diode 124 are formed. Hereinafter, the FEC 102, the CMOS inverter 110, and the pn junction diode 124 will be explained by referring to FIGS. 11 through 13.

Figure 11:
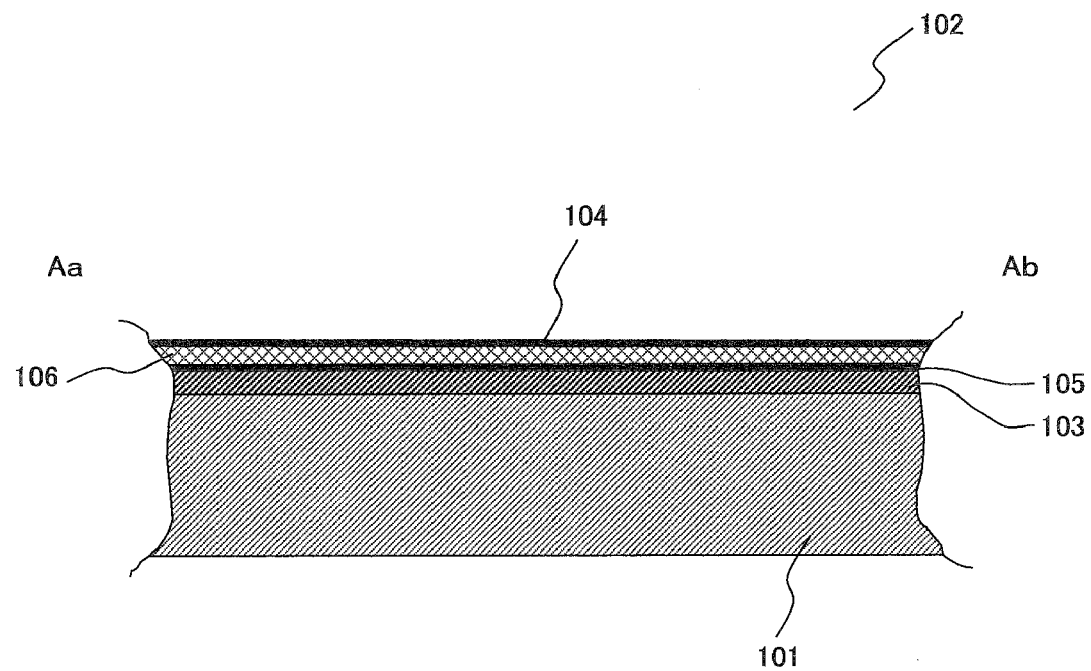
FIG. 11 shows an example of a sectional view (on the plane Aa-Ab) of a ferroelectric thin film capacitor (FEC) 102.

FIG. 11 shows a sectional view (on the plane Aa-Ab) of the FEC 102. This FEC 102 is formed by forming an insulation film (surface oxide film) 103 on the upper surface of the silicon substrate 101, and by forming a bottom electrode 105, a ferroelectric thin film 106, and an upper electrode 104 on the upper surface of the insulation film. For the bottom electrode 105, a Pt or Au thin film with Ti and Cr formed as a buffer layer is used.

Figure 12:
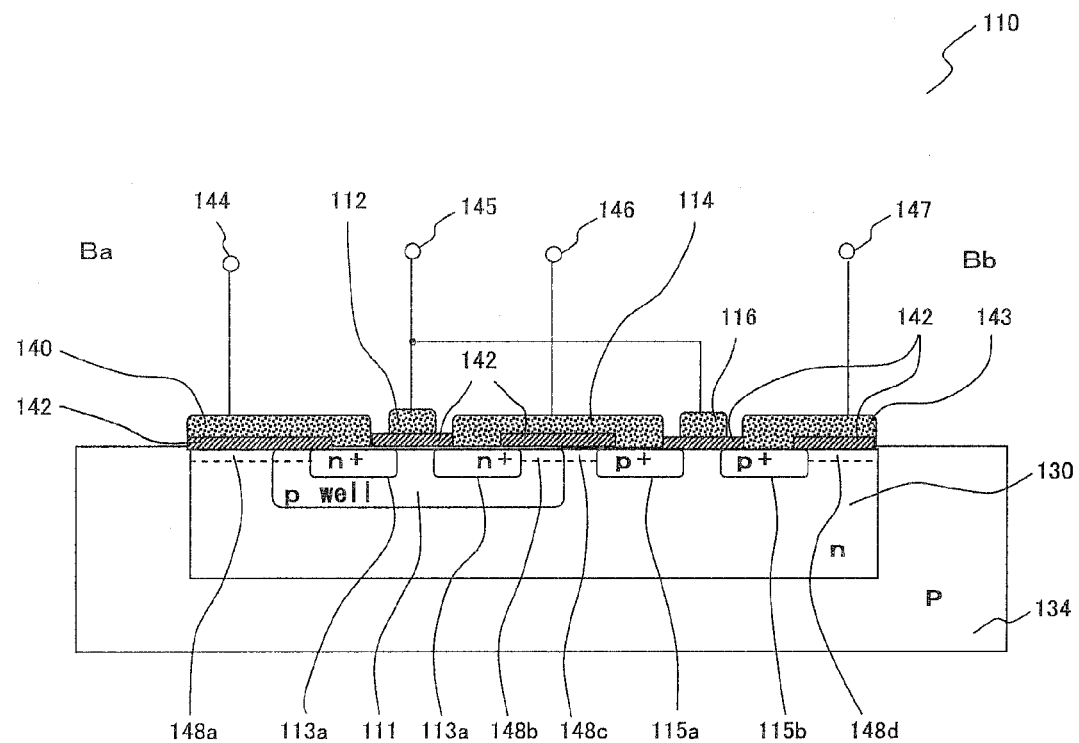
FIG. 12 shows a sectional view (on the plane Ba-Bb) of a CMOS inverter 110.

FIG. 12 shows a sectional view (on the plane Ba-Bb) of the CMOS inverter 110. The configuration of the CMOS inverter 110 is explained as below. On the silicon substrate 101, the p+ diffusion region 134 is formed, and the n diffusion region 130 is also formed. On the n diffusion region 130, a p-well diffusion region 111 is formed, and on the p-well diffusion region 111, n+ diffusion regions 113 (113a and 113b) are formed. Also, on the n diffusion region 130, p+ diffusion regions 115 (115a and 115b) are formed.

The CMOS inverter 110 consists of a p-channel MOSFET (p-MOS) (corresponding to $Q_1$ in FIG. 5) and an n-channel MOSFET (n-MOS) (corresponding to $Q_2$ in FIG. 5). Because an n-MOS is formed in an n-type substrate, an n-type substrate is formed on a p-type region (p well), and an n-MOS ($Q_2$) is formed. In this case, in order to avoid the parasitic MOSFET, n+ regions are provided below a lower side 148a of a source electrode 140 of the n-MOS and a lower side 148b of a bridge electrode serving as an output electrode. Similarly, in the p-MOS ($Q_1$), in order to avoid the parasitic MOSFET, n+ regions are provided below the lower side 148d of the source electrode 120 and the lower side 148c of a bridge electrode serving as an output electrode.

On the upper surface of the n diffusion region 130, insulation films 142 are formed; however, the upper surfaces of the n+ diffusion region 113 (113a and 113b) and the p+ diffusion regions 115 (115a and 115b) are not covered by the insulation films 142.

On the upper surface of the n+ diffusion regions 113a that are not covered by the insulation films 142, an electrode 140 is formed. The upper surface of the n+ diffusion region 113b that is not covered and the upper surface of the p+ diffusion region 115a are electrically continuous with each other via a bridge electrode 114. On the top surface of the p+ diffusion region 115b that is not covered, an electrode 143 is formed. Also, gate electrodes 112 and 116 are formed on the insulation films 142.

An electrode terminal 144 which supplies DC voltage to the CMOS inverter is provided for the electrode 140. An input terminal 145 of the CMOS inverter is provided for the gate electrodes 112 and 116. An output terminal 146 of the CMOS inverter is provided for the bridge electrodes 114. A ground terminal 147 of the CMOS inverter is provided for the electrode 143.

The output terminal 146 corresponds to terminal 16 shown in FIG. 5. The electrode terminal 144 corresponds to terminal 12 shown in FIG. 5. The ground terminal 147 corresponds to terminal 13 shown in FIG. 5.

Figure 13A:
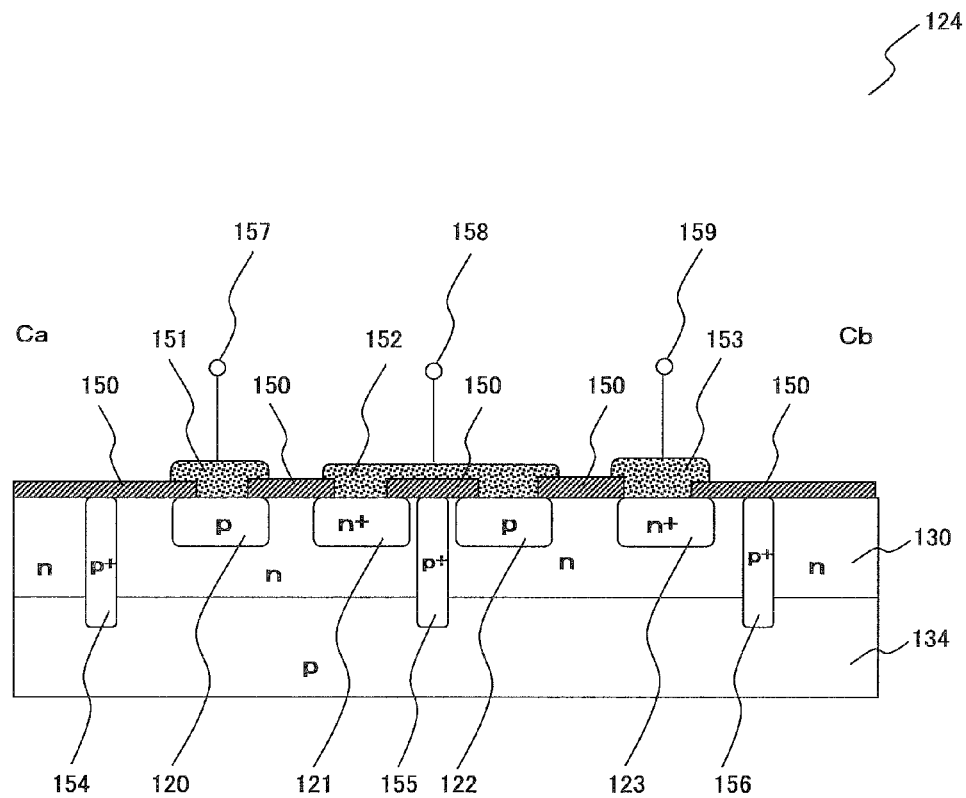
FIG. 13A shows a sectional view (on the plane Ca-Cb) of a pn-junction diode 124.
Figure 13B:
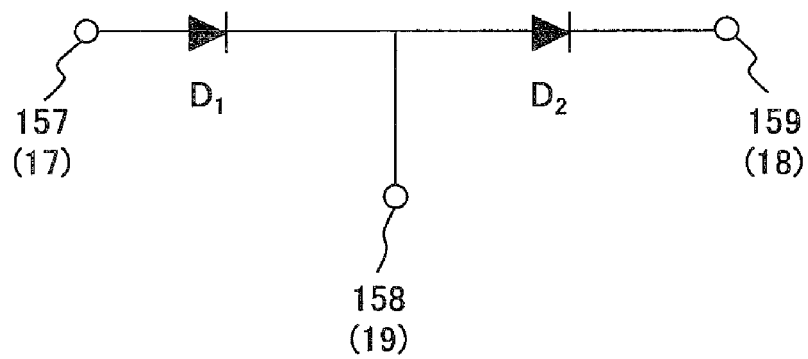
FIG. 13B shows the configuration of FIG. 13A in a simplified manner.

FIG. 13A shows a sectional view (on the plane Ca-Cb) of the pn junction diode 124. FIG. 13B shows the configuration of FIG. 13A in a simplified manner. The configuration of the pn junction diode 124 is explained as below. On the silicon substrate 101, the p+ diffusion region 134 is formed, and the n diffusion region 130 is further formed. On the n diffusion region 130, p diffusion regions 120 and 122 and n+ diffusion regions 121 and 123 are formed. Also, p+ isolation regions 154 and 156 are formed on a part of the n diffusion region 130 and of the p+ diffusion region 134. The upper surfaces of the p diffusion regions 120 and 122 and of the n+ diffusion regions 121 and 123 are not covered by insulation films 150.

On the upper surface of the p diffusion region 120 that is not covered, an electrode 151 is formed. The upper surface of the n+ diffusion region 121 that is not covered and the upper surface of the p+ diffusion region 122 are electrically continuous via a bridge electrode 152. On the top surface of the n+ diffusion region 123 that is not covered, an electrode 153 is formed.

An input terminal 157 is provided for the electrode 151. A common terminal 158 is provided for the bridge electrode 152. An output terminal 159 is provided for the electrode 153.

As shown in FIG. 13B, the input terminal 157 corresponds to the terminal 17 shown in FIG. 5. The common terminal 158 corresponds to the terminal 19 shown in FIG. 5. The output terminal 159 corresponds to the terminal 18 shown in FIG. 5.

FIG. 10 is again referred to. The upper electrode 104 of the FEC 102 and the bridge electrode 152 of the pn junction diode 124 are electrically continuous via an upper electrode wire 125 of the FEC 102. The n+ diffusion region 123 of the pn junction diode 124 is electrically continuous with the p diffusion region 120 of the pn junction diode 124 of the next stage via a connection wire 132.

The bridge electrode 114 and the gate electrodes 112 and 116 of the CMOS inverter 110 are electrically continuous with the bottom electrode 105 via wires 118 and 133. The electrode terminal 144 and a wire 135 which supplies DC voltage to the electrode terminal 144 are connected to each other. A ground terminal 147 of the CMOS inverter 110 and a ground wire 131 are connected to each other.

Hereinafter, a case will be explained by referring to FIGS. 14 through 17 in which a group of cMUT units consisting of a plurality of integrated cMUT elements are arranged in a cylindrical shape. The configuration shown in FIGS. 14 through 17 is only one example of the arrangement, and is not intended to limit the scope of the present invention.

Figure 14:
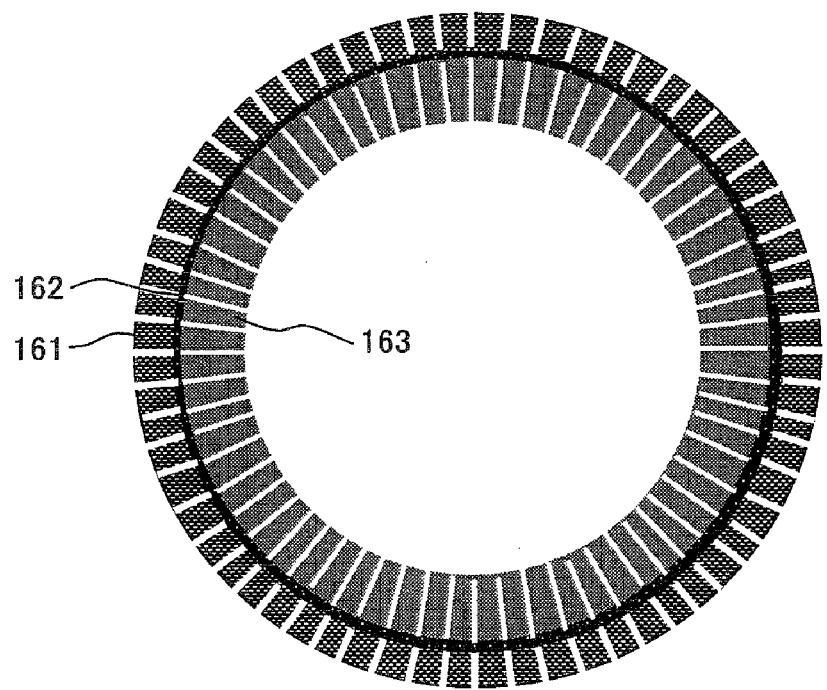
FIG. 14 is a top view of a group of cMUT units arranged in a cylindrical shape.
Figure 15:
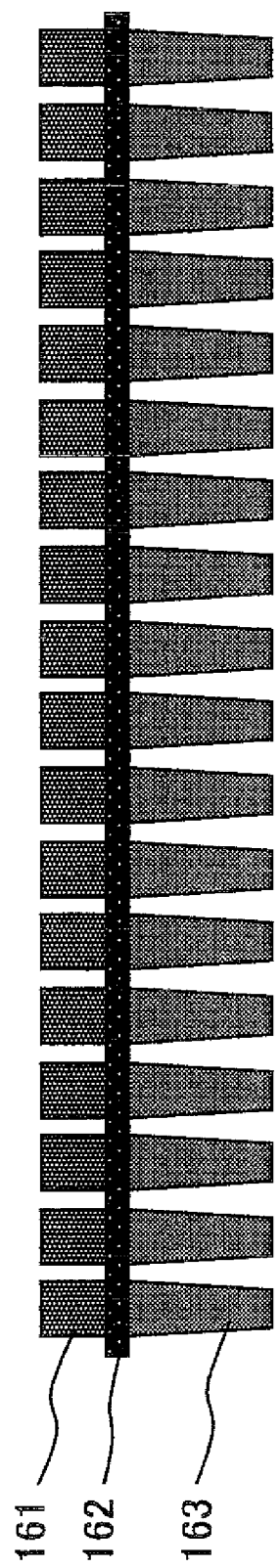
FIG. 15 is a side view of the group of the cMUT units arranged in a cylindrical shape.

FIG. 14 is a top view of the group of cMUT units arranged in a cylindrical shape. FIG. 15 is a side view of the group of cMUT units arranged in a cylindrical shape. Each cMUT unit 161 consists of a plurality (for example, forty-eight) of the cMUT elements. Each element consists of a plurality of the cMUT cells.

The cMUT units 161 are provided on through-hole flexible printed circuit boards (through-hole FPCs) 162. On the bottom surfaces of the through-hole FPCs 162, control circuit units 163 respectively corresponding to the cMUT units 161 are provided. On the through-hole FPCs 162, through holes are made so that the electrodes of the respective elements are connected to the terminal pads for inputting/outputting signals of the control circuit units 163.

When the cMUT units are produced, first, cMUT array units that are in a planar configuration are produced by using the MEMS technique. Next, the cMUT array units and the control circuit unit integration circuits are jointed. Next, the dicing is performed on the cMUT array units and the control circuit unit integration circuits in order to divide them into units. Thereafter, the structure that has undergone the dicing process is rounded into a cylindrical shape.

Figure 16:
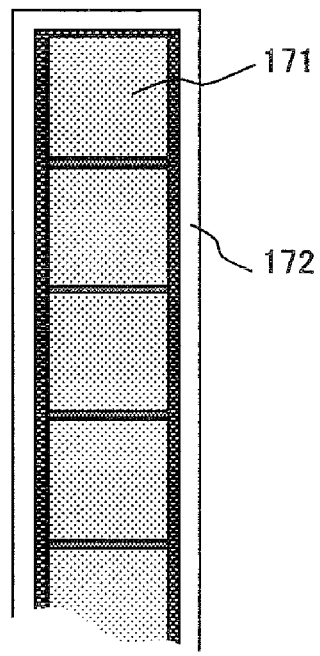
FIG. 16 is an enlarged view showing a cMUT unit 161.

FIG. 16 is an enlarged view showing the cMUT unit 161. The cMUT unit 161 consists of a plurality of cMUT elements 171 provided on a flexible printed circuit board (FPC) 172.

Figure 17:
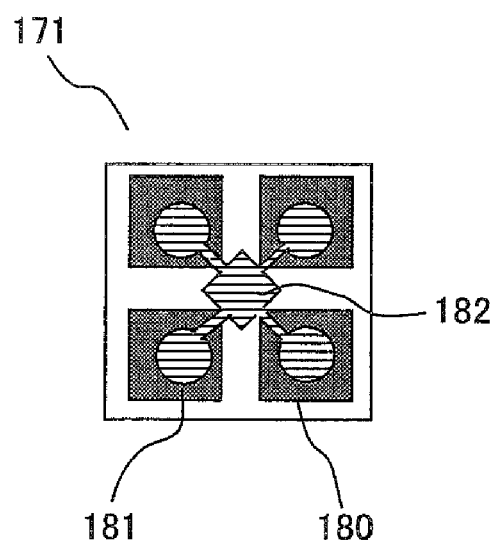
FIG. 17 is an enlarged view showing a cMUT element 171.

FIG. 17 is an enlarged view showing the cMUT element 171. The cMUT element 171 consists of a plurality of transducer cells 180. An electrode 181 is provided for each of the transducer cells 180. The electrodes 181 are connected to the booster circuit.

As described above, in the cMUT according to the present embodiment, a DC high-voltage unit including an input terminal for inputting an alternating-current low voltage, a CMOS inverter circuit, a thin film capacitor, a diode, an output terminal for outputting a DC high-voltage signal, and the like can be formed on one and the same semiconductor substrate. As a result of this, it becomes possible to reduce the size of ultrasonic transducers. Further, it also becomes possible to form an adder, a charge amplifier, a semiconductor switch, a semiconductor switch control unit, and the like on this semiconductor body, and accordingly it becomes possible to further reduce the size.

In the present embodiment, a case has been explained in which a high-voltage generation unit is formed in a cMUT mounted in a body-cavity-insertion diagnostic ultrasound system. However, the scope of the present invention is not limited to this explanation, and it is possible to incorporate the unit into a device such as an ultrasound catheter, an ultrasound capsule endoscope or the like.

Due to the present invention, it becomes possible to reduce the size of capacitive ultrasonic transducer devices that have a DC high-voltage generation unit.

What is claimed is:

1. A capacitive micromachined ultrasonic transducer (cMUT) device, comprising:
a cMUT formed on a semiconductor substrate;
a DC high-voltage generation unit that is provided on the semiconductor substrate and that is for generating a DC high-voltage signal to be superposed on a driving signal for the a cMUT, the DC high-voltage signal having a voltage for energizing the cMUT;
a driving signal generation unit that is provided on the semiconductor substrate and that is for generating the driving signal; and
a superposition unit that is provided on the semiconductor substrate and that is for branching the DC high-voltage signal output from the DC high-voltage generation unit and for superposing one of the branched DC high-voltage signals on the other of the branched DC high-voltage signals via the driving signal generation unit.

2. The cMUT device according to claim 1, wherein: the DC high-voltage generation unit comprises:
an input terminal to which a pre-boosted alternating-current signal for generating the DC high-voltage signal is input;
a CMOS inverter circuit for performing ON/OFF operations on the basis of the low-voltage alternating-current signal input by the input terminal;
a film capacitor that is charged on the basis of the ON/OFF operations performed by the CMOS inverter circuit;
a diode; and
an output terminal from which a DC high-voltage signal obtained by the thin film capacitor is output.

3. The cMUT device according to claim 2, wherein: the film capacitor is a film capacitor that uses a high dielectric constant material.

4. The cMUT device according to claim 3, wherein: the high dielectric material includes a ferroelectric film.

5. The cMUT device according to claim 4, wherein: the ferroelectric film includes a solid solution film containing, as a material, at least one of $BaTiO_3$ and $SrTiO_3$.

6. The cMUT device according to claim 3, wherein: the high dielectric constant material includes a dielectric film that does not contain heavy metal.

7. The cMUT device according to claim 2, wherein: if a group consists of the input terminal, the CMOS inverter circuit, the film capacitor, the diode, and the output terminal, the DC high-voltage generation unit is configured of a multi-stage connection including a plurality of the groups.

8. The cMUT device according to claim 2, wherein: the CMOS inverter circuit is configured of a double diffused MOSFET (DMOSFET).

9. The cMUT device according to claim 2, wherein: the CMOS inverter circuit is configured of a V-groove MOSFET (VMOSFET).

10. The cMUT device according to claim 1, wherein: the cMUT device further comprises:
a charge amplifier provided on the semiconductor substrate;
a semiconductor switch that is provided on the semiconductor substrate and that is for turning ON/OFF electrical continuity between the charge amplifier and the cMUT.

11. The cMUT device according to claim 1, wherein: the driving signal generation unit is configured of a first semiconductor switch, and the first semiconductor switch has an input terminal into which the DC high voltage signal is input, an output terminal from which the DC high voltage signal is output, and a gate into which a signal used for switching a continuation state in the input terminal and the output terminal is input.

12. The cMUT device according to claim 11, wherein: the cMUT device further comprises: a second semiconductor switch that enters an ON state when ultrasound is generated by the cMUT is provided on the semiconductor substrate, and is connected in series with the first semiconductor switch.

13. The cMUT device according to claim 1, wherein: the cMUT further comprises:
a first switching unit switching output levels of the DC high-voltage signal output from the DC high-voltage generation unit;
a driving signal generation unit that is provided on the semiconductor substrate and that is for generating the driving signal;
a superposition unit that is provided on the semiconductor substrate and that is for superposing the driving signal on the DC high-voltage signal;

a second switching unit that is provided on the semiconductor substrate and that controls the driving signal or the DC high-voltage signal being input into the superposition unit; and a third switching unit that is provided on the semiconductor substrate and that controls an ultrasonic reception signal being converted into an electric signal by the cMUT and the converted electric signal being output to an external environment.

14. The cMUT device according to claim 13, wherein: the cMUT further comprises: a switching control unit controlling operations of the first switching unit, the driving signal generation unit, the second switching unit, and the third switching unit.

15. The cMUT device according to claim 1, wherein: the cMUT is configured on a surface of the semiconductor substrate or in the semiconductor substrate.

16. A cMUT array device, wherein: the cMUT according to claim 1 is a capacitive transducer element; and if a group consists of the capacitive transducer element, the DC high-voltage generation unit, a charge amplifier, the driving signal generation unit, a first semiconductor switch that enters an ON state when ultrasound is generated by the cMUT, and a second semiconductor switch that enters an ON state when ultrasound is received by the cMUT, a plurality of the groups are provided on the semiconductor substrate.

17. An ultrasound endoscope scope, comprising: the cMUT array device according to claim 16.

18. A body-cavity-insertion-diagnostic ultrasound system, comprising: the cMUT array device according to claim 16.

19. An ultrasound catheter, comprising: the cMUT array device according to claim 16.

20. An ultrasound capsule endoscope, comprising: the cMUT array device according to claim 16.

21. A method of controlling cMUT device comprising:
a cMUT formed on a semiconductor substrate;
a DC high-voltage generation unit that is provided on the semiconductor substrate and that is for generating a DC high-voltage signal to be superposed on a driving signal for the cMUT, the DC high-voltage signal having a voltage for energizing the cMUT;
a first switching unit switching output levels of the DC high-voltage signal output from the DC high-voltage generation unit;
a driving signal generation unit that is provided on the semiconductor substrate and that is for generating the driving signal;
a superposition unit that is provided on the semiconductor substrate and that is for superposing the driving signal on the DC high-voltage signal;
a second switching unit that is provided on the semiconductor substrate and that controls the driving signal or the DC high-voltage signal being input into the superposition unit; and
a third switching unit that is provided on the semiconductor substrate and that controls an ultrasonic reception signal being converted into an electric signal by the cMUT and the converted electric signal being output to an external environment, wherein:
if ultrasound is to be transmitted from the cMUT device, the first switching unit is driven, and the output level of the DC high-voltage signal is set;
the driving signal generation unit is driven and the driving signal is generated;
the second switching unit is driven so that the driving signal and the DC high-voltage signal are input into the superposition unit; and
the third switching unit is caused to be in an OFF state.

* * * * *